US009119434B2

(12) United States Patent
Stachler et al.

(10) Patent No.: US 9,119,434 B2
(45) Date of Patent: Sep. 1, 2015

(54) EYE PROTECTORS

(75) Inventors: Thomas H. Stachler, Dayton, OH (US);
Mary I. Grilliot, Dayton, OH (US);
William L. Grilliot, Dayton, OH (US)

(73) Assignee: Morning Pride Manufacturing, LLC., Dayton, OH (US)

( * ) Notice: Subject to any disclaimer, the term of this patent is extended or adjusted under 35 U.S.C. 154(b) by 623 days.

(21) Appl. No.: 12/157,539

(22) Filed: Jun. 11, 2008

(65) Prior Publication Data

US 2009/0307818 A1    Dec. 17, 2009

(51) Int. Cl.
*A42B 3/18* (2006.01)
*A61F 9/02* (2006.01)

(52) U.S. Cl.
CPC ............... *A42B 3/185* (2013.01); *A61F 9/025* (2013.01)

(58) Field of Classification Search
USPC ........ 2/410, 5, 6.1, 6.2, 6.3, 6.4, 6.5, 6.6, 6.7,
2/425, 15, 10, 12, 13, 9, 209.13, 175.5,
2/175.6, 426; D2/865, 866, 872, 891,
D2/895; D29/102, 103, 104, 105, 106,
D29/107; 351/155, 156, 157, 47, 48, 57, 58
See application file for complete search history.

(56) References Cited

U.S. PATENT DOCUMENTS

| | | | | |
|---|---|---|---|---|
| 2,481,960 A * | 9/1949 | Wall et al. | | 2/10 |
| 2,725,560 A * | 12/1955 | Feldman | | 2/10 |
| 3,011,170 A * | 12/1961 | Lutz | | 2/13 |
| 3,383,155 A | 5/1968 | Bourke | | |
| 3,383,707 A * | 5/1968 | McNeill | | 2/12 |
| 4,740,069 A * | 4/1988 | Baum | | 351/57 |
| 4,819,274 A * | 4/1989 | Day | | 2/10 |
| 5,129,102 A * | 7/1992 | Solo | | 2/10 |
| 5,412,812 A * | 5/1995 | Gatchalian | | 2/10 |
| 5,422,686 A * | 6/1995 | Kelman et al. | | 351/155 |
| 5,533,208 A * | 7/1996 | Tonoyan et al. | | 2/10 |
| 5,689,827 A * | 11/1997 | Ryder | | 2/10 |
| 5,826,271 A * | 10/1998 | Garrett | | 2/10 |
| 6,237,147 B1 * | 5/2001 | Brockman | | 2/10 |
| 2006/0109420 A1 * | 5/2006 | Holm | | 351/153 |

OTHER PUBLICATIONS

U.S. Appl. No. 11/974,654, filed Oct. 15, 2007, Stachler et al.
U.S. Appl. No. 12/157,483, filed Jun. 11, 2008, Stachler et al.
U.S. Appl. No. 12/157,485, filed Jun. 11, 2008, Stachler et al.

* cited by examiner

*Primary Examiner* — Katherine Moran
(74) *Attorney, Agent, or Firm* — Wood, Phillips, Katz, Clark & Mortimer

(57) ABSTRACT

A protective helmet (10) of the type worn by a firefighter or other emergency worker has a crown (12) and a brim (14) that projects forwardly and laterally from the lower part of the crown (12). An eye protector (16) is provided on the helmet (10) in the form of a pair of transparent eye shields (18) that are mounted to the underside of the brim (14) by a bracket (20) for manual movement between a storage position and the usage position. A snap fit connector or hinge is provided on either the bracket (20) or each of the eye shields (18) to pivotably connect the eye shields to the bracket (20) for movement between the storage and usage positions.

16 Claims, 3 Drawing Sheets

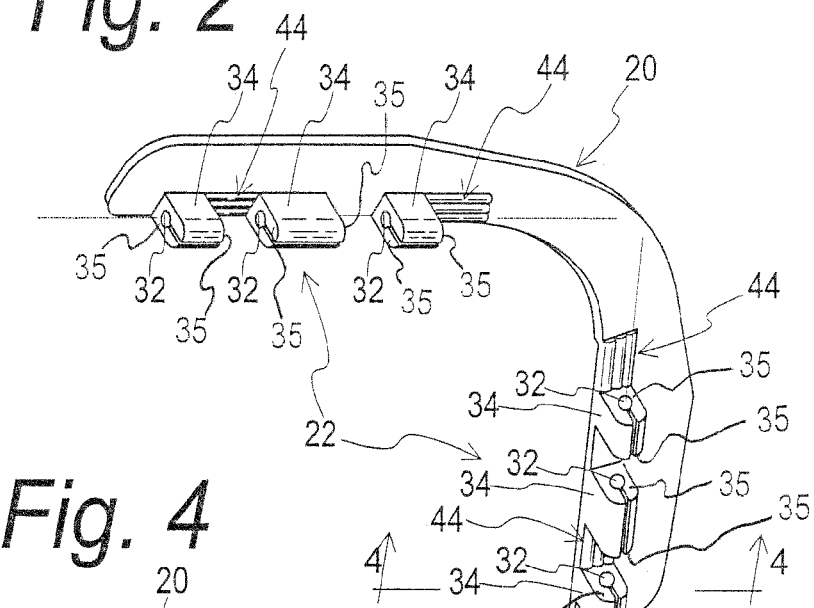
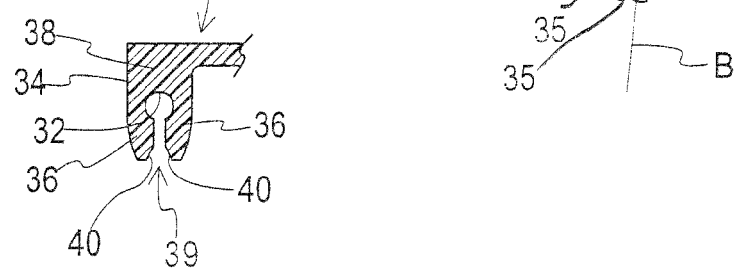
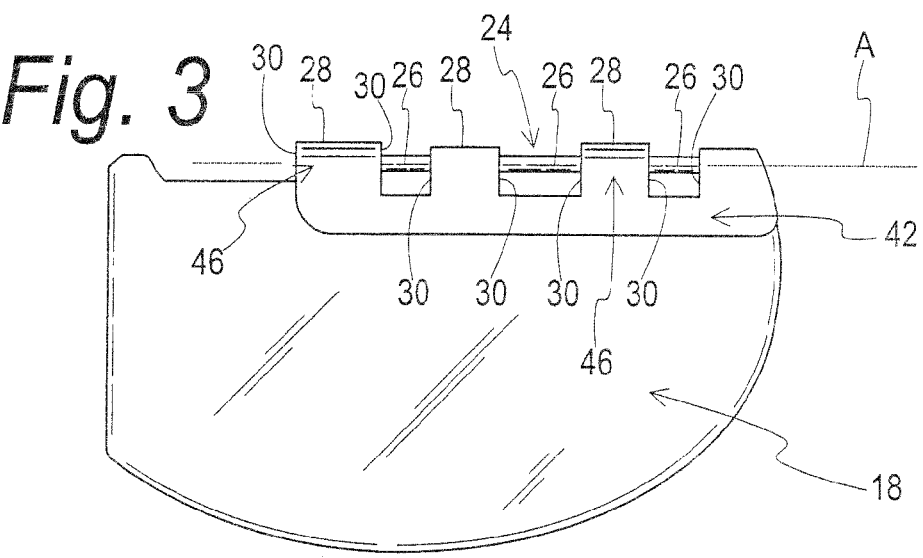

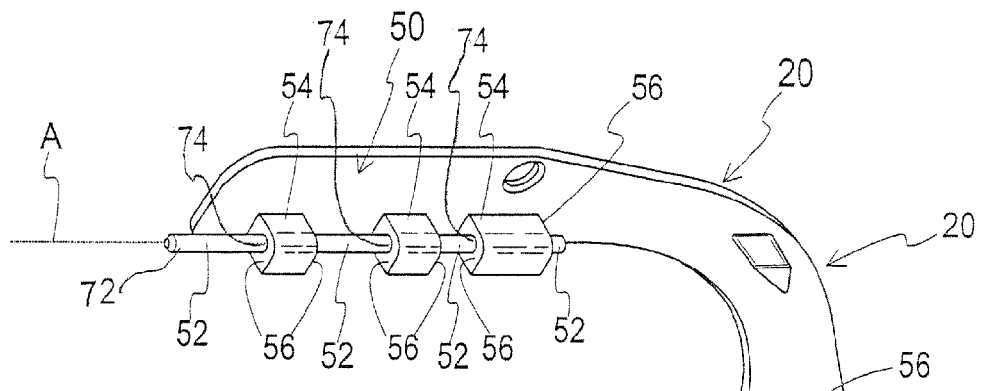
Fig. 5
Fig. 7A  Fig. 7B
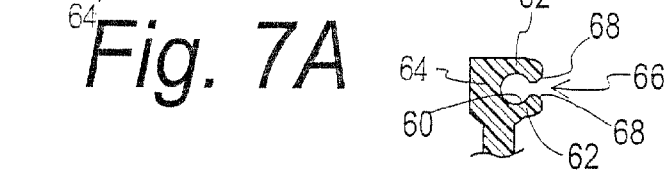
Fig. 6
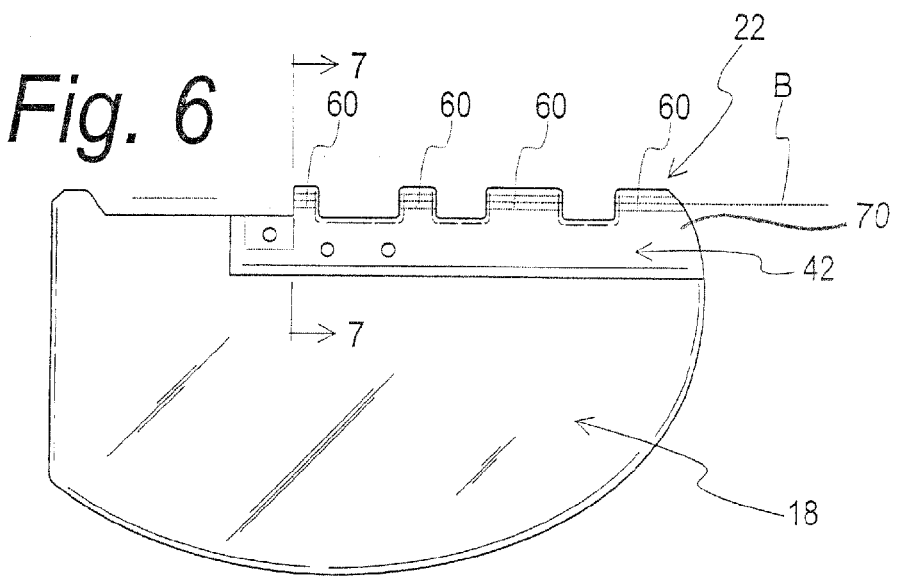

EYE PROTECTORS

CROSS-REFERENCE TO RELATED APPLICATIONS

Not Applicable.

FEDERALLY SPONSORED RESEARCH OR DEVELOPMENT

Not Applicable.

MICROFICHE/COPYRIGHT REFERENCE

Not Applicable.

FIELD OF THE INVENTION

This invention pertains to eye protectors for use with a helmet for a firefighter or other emergency rescue worker.

BACKGROUND OF THE INVENTION

Commonly, a helmet for a firefighter or for an industrial, chemical, or emergency rescue worker has a crown and a brim, which projects forwardly from the crown and which may project in other directions from the crown. Commonly, the helmet is equipped with a pair of eye shields, one for each eye of a wearer, and each of the pair of eye shields is adapted to be manually moved between a storage position and a usage position. In the usage position, but not in the storage position, the eye shield projects downwardly so as to shield a given eye of a wearer against sparks, liquids, particles, and other objects striking the front of the eye shield.

An example of an eye shield, as described in the preceding paragraph, is disclosed in U.S. Pat. No. 3,383,155 to Lester T. Bourke. As disclosed in U.S. Pat. No. 3,383,155, the disclosure of which is incorporated herein by reference, each of the pair of eye shields is mounted to a helmet, beneath a brim projecting forwardly from a crown of the helmet, and each of the pair of eye shields is adapted to be manually flipped between the storage and usage positions and is stable in either of the storage and usage positions. Similar eye shields are available commercially from various sources including Morning Pride Manufacturing, L.L.C. of Dayton, Ohio. While these shields have performed well for their intended purpose, there is always room for improvement.

SUMMARY OF THE INVENTION

In accordance with one feature of the inventions, an eye protector is mountable to a protective helmet for use by a firefighter or other emergency worker, the protective helmet having a brim. The eye protector includes a bracket mounted to the brim, an eye shield movable between a storage position extending along the brim and a usage position extending downward from the brim to shield the eye of a wearer, and a snap fit connector on one of the bracket and eye shield to pivotably connect the eye shield to the bracket for movement between the storage and usage positions.

As one feature, the eye protector further includes a journal on the other of the bracket and eye shield, the journal received in the snap fit connector to connect the eye shield to the bracket for movement between the storage and usage positions.

In one feature, the journal includes a cylindrical element on the other of the bracket and eye shield.

According to one feature, the journal includes plural cylindrical elements of the bracket and eye shield.

As one feature, the journal is formed as a unitary part of the other of the bracket and eye shield.

In one feature, the snap fit connector includes a bearing surface having a U-shaped transverse cross-section.

According to one feature, the snap fit connector includes plural bearing surfaces, each of the bearing surfaces having a U-shaped transverse cross-section and receiving a corresponding one of the cylindrical elements.

As one feature, the snap fit connector is formed as a unitary part of the one of the bracket and eye shield.

In accordance with one feature of the invention, an eye protector is mountable to a protective helmet for use by a firefighter or other emergency worker, the protective helmet having a brim. The eye protector includes a bracket mounted to the brim, a pair of eye shields movable between a storage position extending along the brim and a usage position extending downward from the brim to shield the eyes of a wearer, and a pair of snap fit connectors on one of the bracket and the pair of eye shield to pivotably connect the eye shields to the bracket for movement between the storage and usage positions.

In one feature, the eye protector further includes a pair of journals on the other of the bracket and the pair of eye shields, each of the journals received in a corresponding one of the snap fit connectors to connect the eye shield to the bracket for movement between the storage and usage positions.

As one feature, the journals comprise a pair of cylindrical elements on the other of the bracket and the pair of eye shields.

According to one feature, each journal includes plural cylindrical elements.

In one feature, the journals are formed as a unitary part of the other of the bracket and the pair of eye shields.

In accordance with one feature, each of the snap fit connectors includes a bearing surface having a U-shaped transverse cross-section.

As one feature, each of the snap fit connectors includes plural bearing surfaces, each of the bearing surfaces having a U-shaped transverse cross-section and receiving a corresponding one of the cylindrical portions.

In one feature, the pair of snap fit connectors are formed as a unitary part of the one of the bracket and the pair of eye shields.

In accordance with one feature of the invention, an eye protector is mountable to a protective helmet for use by a firefighter or other emergency worker, the protective helmet having a brim. The eye protector includes a bracket mounted to the brim, an eye shield movable between a storage position extending along the brim and a usage position extending downward from the brim to shield the eye of a wearer, a snap fit connector on one of the bracket and eye shield to pivotably connect the eye shield to the bracket for movement between the storage and usage positions, and a journal on the other of the bracket and eye shield, the journal received in the snap fit connector to connect the eye shield to the bracket for movement between the storage and usage positions. At least one of the journal and the snap fit connector is formed as a unitary part of the corresponding one of the bracket and eye shield.

As one feature, the journal includes a cylindrical portion of the other of the bracket and eye shield.

In one feature, the journal includes plural cylindrical portions of the other of the bracket and eye shield.

According to one feature, the snap fit connector includes a bearing surface having a U-shaped transverse cross-section.

As one feature, the snap fit connector includes plural bearing surfaces, each of the bearing surfaces having a U-shaped transverse cross-section and receiving a corresponding one of the cylindrical portions.

In accordance with one feature, the snap fit connector is a unitary part of the bracket and the journal is a unitary part of the eye shield.

According to one feature, the snap fit connector is a unitary part of the eye shield and the journal is a unitary part of the bracket.

Other objects, features, and advantages of the invention will become apparent from a review of the entire specification, including the appended claims and drawings.

BRIEF DESCRIPTION OF THE DRAWINGS

FIG. 2 is a perspective view of a bracket component of the eye protector of FIG. 1;

FIG. 3 is a front view of an eye shield of the eye protector of FIG. 1;

FIG. 4 is an enlarged, partial section view taken along lines 44 in FIG. 3;

FIG. 5 is a perspective view of another embodiment of a bracket of the eye protector of FIG. 1;

FIG. 6 is a front view of another embodiment of an eye shield of the eye protector of FIG. 1; and FIGS. 7A and 7B are enlarged, partial section views taken along lines 7-7 in FIG. 6.

DETAILED DESCRIPTION OF THE PREFERRED EMBODIMENT

Figure 1:
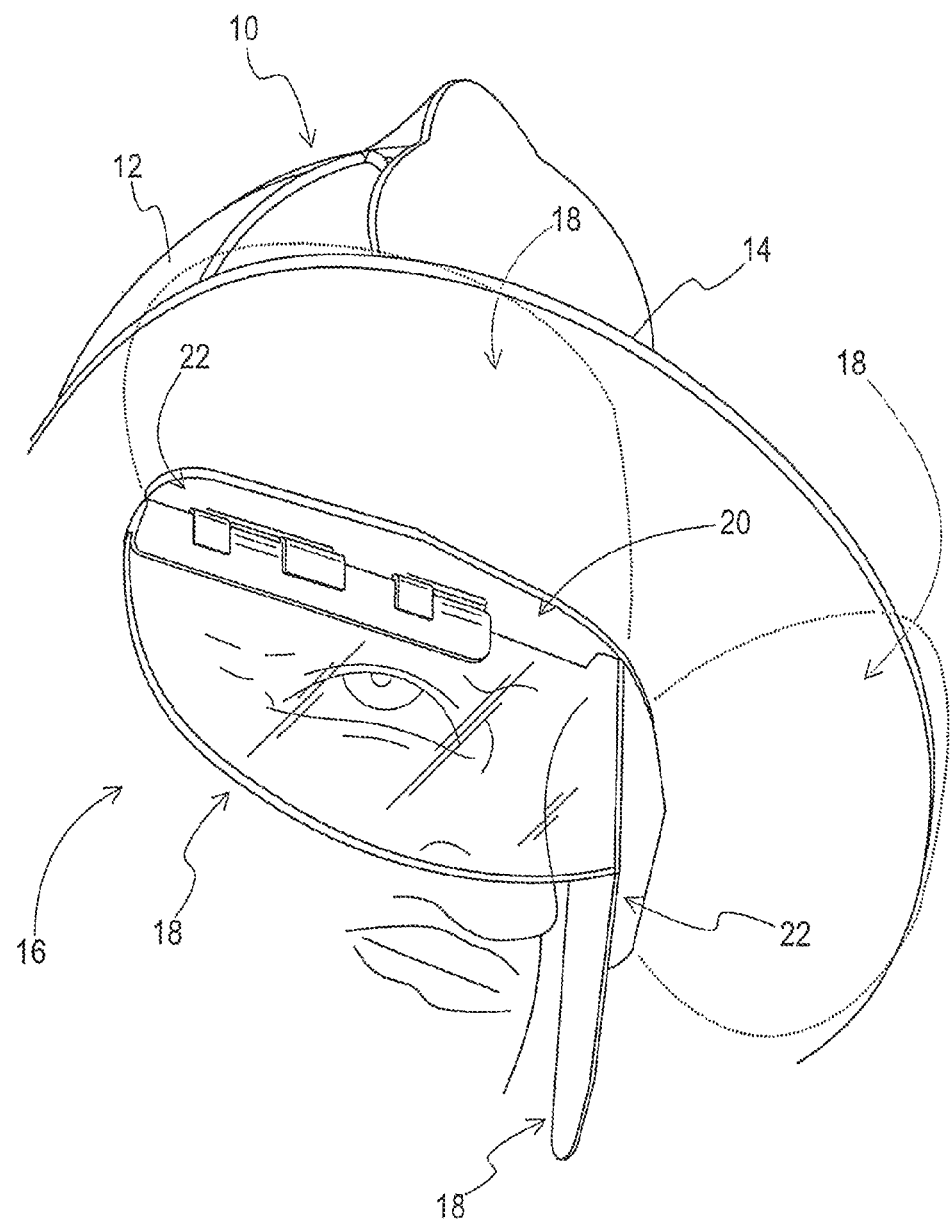
FIG. 1 is a fragmentary, perspective view looking upward toward the front of a helmet equipped with an eye protector embodying the invention.

As shown in FIG. 1, a protective helmet 10 of the type worn by a firefighter or other emergency worker has a crown 12 and a brim 14 that projects forwardly and laterally from the lower part of the crown 12. An eye protector 16 is provided on the helmet 10 in the form of a pair of transparent eye shields 18 that are mounted to the underside of the brim 14 by a bracket 20 for manual movement between a storage position and a usage position. The shields 18 are shown in the usage position in FIG. 1, with each shield 18 extending downward from the brim 14 to shield the eyes of a wearer against sparks, liquids, particles, and other such objects which will strike the front of the shields 18 rather than the eyes of a wearer. In the storage position, each of the shields 18 project forwardly along and beneath the brim 14, as shown in phantom in FIG. 1. As shown generally at 22, a snap fit connector or hinge is provided on either the bracket 20 or each of the eye shields 18 to pivotably connect the eye shields 18 to the bracket 20 for movement between the storage and usage position.

With reference to the embodiment of the eye protector 16 shown in FIGS. 2 and 3, each of the eye shields 18 (only one shown in FIG. 3) includes a journal 24 in the form of a plurality of cylindrical elements 26. Preferably, each of the cylindrical elements 26 is separated by a spacer element 28, with shoulders 30 provided on the ends of the spacer elements 28 transverse to the longitudinal axis A of the cylindrical elements 26. The snap fit connector 22 includes a plurality of bearing surfaces 32 defined in connector or hinge elements 34 on the bracket 20, with each of the bearing surfaces 32 having a U-shaped or cylindrical-shaped transverse cross-section that is shaped to receive and conform to a corresponding one of the cylindrical elements 26. Shoulders 35 are provided on the ends of each of the connector elements 34 transverse to the longitudinal axis B. As best seen in FIG. 4, each U-shaped transverse cross-section is defined by a pair of legs 36 that extend upwardly from a base 38 to further define an opening 39 that is preferably narrower than the transverse thickness of the corresponding cylindrical element 26 so as to retain the cylindrical element 26 within the snap fit connector 22 after assembly. In this regard, it is preferred that a pair of chamfers 40 be provided on each of the legs to assist in assembling the cylindrical elements 26 into the snap fit connector 22.

In the embodiment of FIGS. 2 and 3, each of the eye shields 18 is a one piece, unitary construction with each of the cylindrical elements 26 and spacer elements 28 formed as a unitary part of the eye shield 18, preferably by a suitable forming process, such as suitable molding and/or machining process. Similarly, the bracket 20 is a one piece, unitary construction with the features 32, 34, 36 and 38 being formed as a unitary part of the bracket 20 using a suitable forming process, such as a suitable molding and/or machine process. Furthermore, as best seen in FIG. 3, it may be desirable for the areas 42 adjacent the cylindrical elements 26 and spacer elements 28 to be of a thicker cross section than the remainder of the eye shield 18 to improve the structural integrity of the eye shield 18. No separate fasteners are required, or directed into, any of the cylindrical elements 26, the spacer elements 28, the eye shield 18, the hinge elements 34, or base 38, to: a) secure the cylindrical elements 26 and spacer elements 28 to the eye shield 18; or b) secure the hinge elements 34 to the base 38.

As best seen in FIG. 2, the bracket also preferably includes one or more frictional lock features 44 that engage corresponding lock features 46 on the lens in both the usage and storage positions to retain the eye shield 18 in each position.

FIGS. 5 and 6 illustrate another embodiment of the eye protector 16 wherein a snap connector 22 is provided on each of the eye shields 18 rather than on the bracket 20. In this regard, the bracket 20 includes a pair of journals 50, each journal 50 to be received in the snap fit connector 22 of a corresponding one of the eye shields 18. Each of the journals 50 is provided in the form of a plurality of cylindrical elements 52, with each of the cylindrical elements 52 being separated by a spacer element 54, with shoulders 56 provided on the ends of the spacer elements 54 transverse to the longitudinal axis A of the cylindrical elements 52. Each of the snap fit connectors 22 includes a plurality of bearing surfaces 60 on the corresponding eye shield 18, with each of the bearing surfaces 60 having a U-shaped or cylindrical-shaped transverse cross-section that is shaped to receive and conform to a corresponding one of the cylindrical elements 52. As best seen in FIGS. 7A and 7B, the U-shaped transverse cross-section is defined by a pair of legs 62 that extend upwardly (FIG. 7A) or rearwardly (FIG. 7B) from a base 64 to further define an opening 66 that is preferably narrower than the transverse thickness of the corresponding cylindrical element 52 so as to retain the cylindrical element 52 within the snap fit connector 22 after assembly. It is preferred that a pair of chamfers 68 be provided on each of the legs to assist in assembling the cylindrical elements into the snap fit connector.

While the embodiments of FIGS. 5 and 6 can be formed as one piece, unitary constructions in the same manner as described for the embodiments of FIGS. 3 and 4, an alternate construction is illustrated in FIGS. 5 and 6 wherein the snap fit connector 22 is formed as a separate component 70 that is then bonded or fastened to a unitary piece that forms the remainder of the eye shield 18. For the bracket 20, the cylindrical elements 52 are defined by a pair of cylindrical rods 72, that are interference fit through conforming cylindrical openings 74 formed in each of the spacer elements 54.

The invention claimed is:

1. An eye protector mountable to a protective helmet for use by a firefighter or other emergency worker, the protective helmet having a brim, the eye protector comprising:
- a bracket mounted to the brim;
- a pair of eye shields movable between a storage position extending along the brim and a usage position extending downward from the brim to shield the eyes of a wearer;
- a pair of snap fit connectors on one of the bracket and the pair of eye shields to pivotably connect the eye shields to the bracket for movement between the storage and usage positions; and
- a pair of journals on the other of the bracket and the pair of eye shields, each of the journals received in a corresponding one of the snap fit connectors to connect the eye shield to the bracket for movement between the storage and usage positions;
- wherein the bracket defines one of the: a) pair of journals; and b) pair of snap fit connectors,
- wherein there is a single piece that defines at least a part of at least one of the eye shields and the other of the: a) pair of journals; and b) pair of snap fit connectors so that no separate fastener is used to secure the other of the: a) pair of journals; and b) pair of snap fit connectors to the at least one eye shield; and
- wherein each of the snap fit connectors comprises a bearing surface having a U-shaped transverse cross-section receiving one of the journals.

2. The eye protector of claim 1 wherein the journals comprise a pair of cylindrical elements.

3. The eye protector of claim 1 wherein each journal comprises plural cylindrical elements.

4. The eye protector of claim 3 wherein each of the snap fit connectors comprises plural bearing surfaces, each of the bearing surfaces having a U-shaped transverse cross-section and receiving a corresponding one of the cylindrical portions.

5. The eye protector of claim 1 wherein the journals are a unitary part of the bracket.

6. The eye protector of claim 1 wherein the pair of snap fit connectors are a unitary part of the bracket.

7. The eye protector according to claim 1 wherein there are cooperating lock features on the bracket and the pair of eye shields to selectively releasably retain the pair of eye shields in each of the usage and storage positions.

8. The eye protector according to claim 7 wherein one of the eye shields has first and second spacers between which one of the journals resides and the lock feature on the eye shields is on one of the first and second spacers.

9. An eye protector mountable to a protective helmet for use by a firefighter or other emergency worker, the protective helmet having a brim, the eye protector comprising:
- a bracket mounted to the brim;
- an eye shield movable between a storage position extending along the brim and a usage position extending downward from the brim to shield the eye of a wearer;
- a snap fit connector on one of the bracket and eye shield to pivotably connect the eye shield to the bracket for movement between the storage and usage positions; and
- a journal on the other of the bracket and eye shield, the journal received in the snap fit connector to connect the eye shield to the bracket for movement between the storage and usage positions;
- wherein the journal and the snap fit connector each comprises one piece that defines at least a part of the corresponding one of the bracket and eye shield so that no separate fastener is used to secure: a) the snap fit connector to the one of the bracket and eye shield; and b) the journal to the other of the bracket and eye shield; and
- wherein the snap fit connector comprises a bearing surface having a U-shaped transverse cross-section receiving the journal.

10. The eye protector of claim 9 wherein the journal comprises a cylindrical portion.

11. The eye protector of claim 10 wherein the journal comprises plural cylindrical portions.

12. The eye protector of claim 11 wherein the snap fit connector comprises plural bearing surfaces, each of the bearing surfaces having a U-shaped transverse cross-section and receiving a corresponding one of the cylindrical portions.

13. The eye protector of claim 9 wherein the snap fit connector is a unitary part of the bracket and the journal is a unitary part of the eye shield.

14. The eye protector of claim 9 wherein the snap fit connector is a unitary part of the eye shield and the journal is a unitary part of the bracket.

15. The eye protector according to claim 9 wherein there are cooperating lock features on the bracket and eye shield to selectively, releasably retain the eye shield in each of the storage and usage positions.

16. The eye protector according to claim 15 wherein the eye shield has a spacer that connects to the journal and the lock feature on the eye shield is on the spacer.

* * * * *